(12) United States Patent
Sauer et al.

(10) Patent No.: US 7,327,822 B2
(45) Date of Patent: Feb. 5, 2008

(54) METHODS, APPARATUS, AND SOFTWARE FOR RECONSTRUCTING AN IMAGE

(75) Inventors: Ken David Sauer, South Bend, IN (US); Charles Addison Bouman, West Lafayette, IN (US); Jiang Hsieh, Brookfield, WI (US); Jean-Baptiste Thibault, Milwaukee, WI (US)

(73) Assignees: Purdue Research Foundation, West Lafayette, IN (US); University of Notre Dame du Lac, Notre Dame, IN (US); General Electric Company, Schenectady, NY (US)

( * ) Notice: Subject to any disclaimer, the term of this patent is extended or adjusted under 35 U.S.C. 154(b) by 352 days.

(21) Appl. No.: 11/185,477

(22) Filed: Jul. 20, 2005

(65) Prior Publication Data

US 2007/0019777 A1   Jan. 25, 2007

(51) Int. Cl.
*A61B 6/03* (2006.01)
(52) U.S. Cl. .................. 378/4; 378/901; 382/131
(58) Field of Classification Search ............. 378/4, 378/901; 382/131
See application file for complete search history.

(56) References Cited

U.S. PATENT DOCUMENTS

| 6,768,782 B1 | 7/2004 | Hsieh et al. |
| 6,907,102 B1 | 6/2005 | Sauer et al. |
| 2004/0028264 A1 * | 2/2004 | Kalifa ............... 382/131 |

OTHER PUBLICATIONS

Thibault et al., High Quality Iterative Image Reconstruction for Multi-Slice Helical CT, Proceedings of the VII International Conference on Fully 3D reconstruction in Radiology and Nuclear Medicine, Jun. 29-Jul. 4, 2003, Saint Malo, France, pp. 51-54.*
Villian et al., Computed Tomography Image Restoration using Convex-Potential 3-D Markov Random Fields, Oct. 30-Nov. 2, 1997, Proceedings of the 19th International Conference—IEEE/EMBS, pp. 561-564.*
Allain et al., Regularized Approach in 3D Helical Computed Tomography, Oct. 23-26, 2002, Proceedings of the Second Joint EMBS/BMES Conference, pp. 943-944.*
Charles Addison Bouman et al.; Methods, Apparatus, and Software for Reconstructing an Image; U.S. Appl. No. 10/991,176, filed Nov. 17, 2004; 22 pgs.
Bouman et al.; A Unified Approach to Statistical Tomography Using Coordinate Descent Optimization; IEEE Trans. on Image Processing, vol. 5, No. 3, pp. 480-492, Mar. 1996, 30 pgs.
Thibault et al.; High Quality Iterative Image Reconstruction for Multi-Slice Helical CT; GE Medical Systems, Waukesha, WI 53188; 4 pgs.

* cited by examiner

*Primary Examiner*—Edward J. Glick
*Assistant Examiner*—John M Corbett
(74) *Attorney, Agent, or Firm*—Armstrong Teasdale LLP

(57) ABSTRACT

A method of reconstructing an image includes combining a two-dimensional forward projection function and a three-dimensional stabilizing function to generate an iterative reconstruction algorithm, and using the obtained iterative reconstruction algorithm to perform a multislice Computed Tomography (CT) reconstruction to generate an image.

20 Claims, 2 Drawing Sheets

METHODS, APPARATUS, AND SOFTWARE FOR RECONSTRUCTING AN IMAGE

BACKGROUND OF THE INVENTION

This invention relates generally to methods, apparatus and software for image reconstruction in computed tomography and, more particularly, to methods, apparatus and software for iterative reconstruction techniques.

Multi-slice detector arrays provide data for multiple adjacent image slices. With data organized into sets, each of which pertains to a single plane, these slices are usually reconstructed independently of each other with backprojection techniques. Image reconstruction from CT scan data benefits from iterative reconstruction techniques in cases of limited numbers of measurements for a given volume, and for limited X-ray dosage resulting in high noise in measurements. Applying iterative reconstruction separately to data sets for individual planes may not, however, yield adequate results in the most challenging cases.

BRIEF DESCRIPTION OF THE INVENTION

In one aspect, a method of reconstructing an image is provided. The method includes combining a two-dimensional forward projection function and a three-dimensional stabilizing function to generate an iterative reconstruction algorithm, and using the obtained iterative reconstruction algorithm to perform a multislice Computed Tomography (CT) reconstruction to generate an image.

In another aspect, an imaging system is provided. The imaging system includes a radiation source, a detector array including a plurality of cells positioned to receive radiation from the source, and a computer coupled to the detector array. The computer is configured to combine a two-dimensional forward projection function and a three-dimensional stabilizing function to generate an iterative reconstruction algorithm, and use the obtained iterative reconstruction algorithm to perform a multislice Computed Tomography (CT) reconstruction to generate an image.

In a further aspect, a computer readable medium encoded with a program is provided. The program is configured to instruct a computer to combine a two-dimensional forward projection function and a three-dimensional stabilizing function to generate an iterative reconstruction algorithm, and use the obtained iterative reconstruction algorithm to perform a multislice Computed Tomography (CT) reconstruction to generate an image.

DETAILED DESCRIPTION OF THE INVENTION

Figure 1:
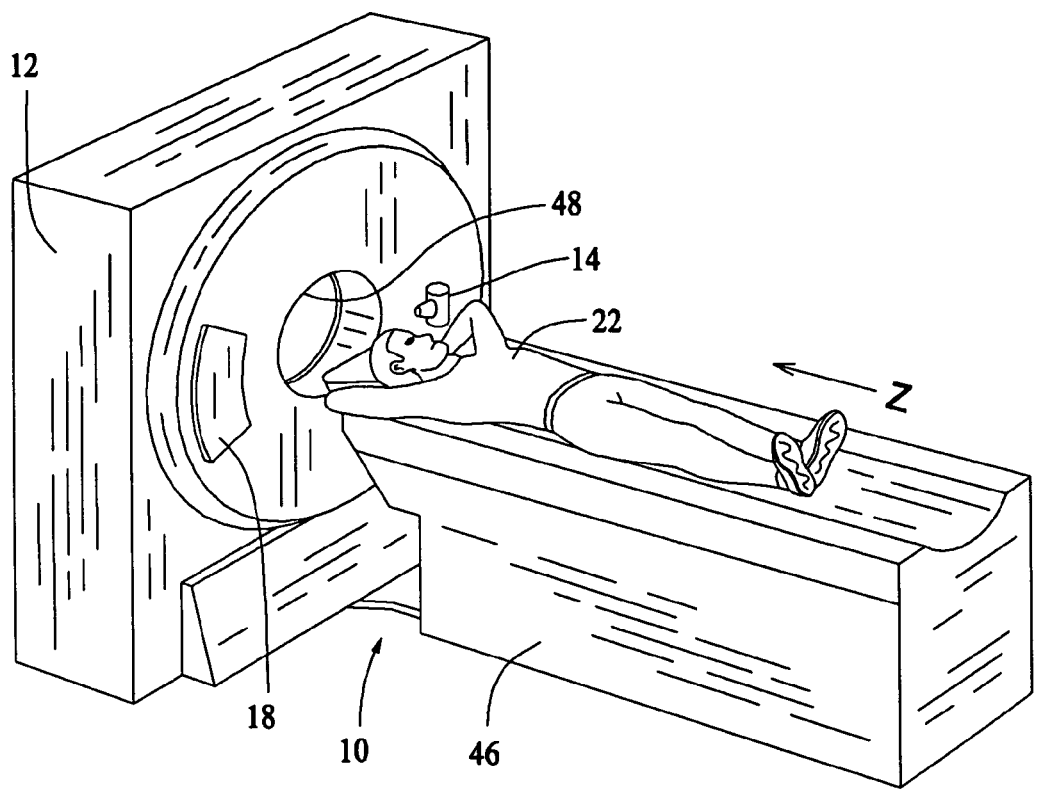
FIG. 1 is a pictorial view of a CT imaging system embodiment.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

To further improve the data acquisition, a multi-slice or volumetric CT system may be utilized. Such systems collect multiple projections simultaneously by using a detector that includes a plurality of detector rows. In such configurations, the fan beam geometry becomes a cone beam geometry.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also, as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 2:
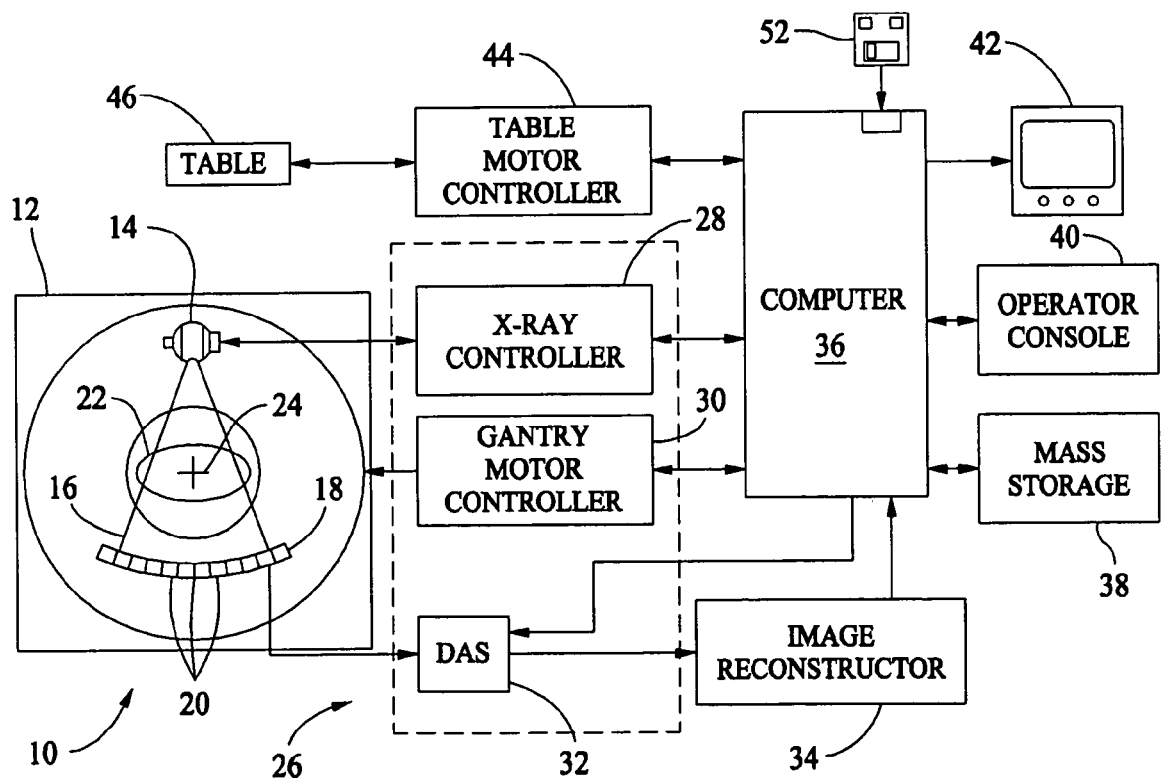
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Generally, a processor in at least one of DAS 32, reconstructor 34, and computer 36 shown in FIG. 2 is programmed to execute the processes described below. Of course, the embodiments described herein are not limited to practice in CT system 10 and can be utilized in connection with many other types and variations of imaging systems. In one embodiment, computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, field programmable gate arrays (FPGA) and all other programmable circuits.

Herein described are new methods, apparatus, and software for accurate geometric forward modeling of third generation CT scanners that is suitable for iterative reconstruction of high quality clinical images for medical diagnostic purposes. The herein described methods support all configurations of CT scanners, including single-slice and multi-slice CT, as well as any trajectory of acquisition, such as step-and-shoot (axial) mode, helical mode, or any other mode, with constant or varying pitch and sampling patterns.

Traditionally, images have been reconstructed from computed tomography (CT) data using so-called direct reconstruction algorithms such as filtered back projection (FBP) or convolution back projection (CBP), for example. Recently, iterative reconstruction (IR) algorithms have been introduced for the reconstruction of CT images. One advantage of utilizing an IR algorithm is that the IR algorithm can more accurately model the measurements obtained from real CT systems. This is particularly true for helical CT systems that include multi-slice detectors because these systems produce projection measurements that pass obliquely through the 2-D reconstructed image planes. By more accurately modeling these projections, IR algorithms can generate images having higher quality, lower noise, and fewer artifacts.

For example, utilizing a helical scan CT system, the X-ray source and the detector array rotate around the object being scanned. If a helical CT scanner is utilized, then the X-ray source and detector also move in the direction perpendicular to the plain of rotation tracing out a generally helical path. At periodic moments in time, the detector array measures the X-ray energy that passes through the object. Each such measurement is known as a view. Generally, the detector array includes a plurality of detector elements that are arranged along the direction of rotation, referred to herein as channels. In addition, a multislice CT scanner also includes a plurality of rows. For example, a four slice detector includes four rows of detector elements, wherein each row includes a plurality of channels.

For a single rotation of the scanner, denote the detector measurements from the kth row of the detector are defined as $y_k = \{y_{ki}\}_{i=0}^{M-1}$, where M is the total number of measurements obtained from a single row of the detector in a single rotation, and $y_k$ is defined as a single slice of the data, and the entire set of data is defined as $y = \{y_k\}_{k=0}^{K_1-1}$, where $K_1$ is the number of slices in the detector.

Alternatively, $y_k$ may be a set of data, extracted from a plurality of detector rows in helical scans, which is used to construct an image on a conventional image plane, or a plane oblique to horizontal and/or vertical axes.

The volume being reconstructed is then discretized into voxels arranged along three dimensions, wherein the first two dimensions are generally oriented to be in the plane of rotation, and the third dimension is generally oriented perpendicularly, or approximately perpendicularly, to the plane of rotation. For example, $x_{ki}$ is defined as the voxel where k indexes the position along the third dimension and i indexes the specific voxel in the plane. Further, $x_k = \{x_{ki}\}_{i=0}^{N-1}$ is defined as the set of voxels in the kth plane, and the entire set of planes being reconstructed is defined as $x = \{x_k\}_{k=0}^{K_2-1}$, where $K_2$ is the number of planes in the volume.

Accordingly, the forward model for the scanner is the function which yields the expected measurement when forward projecting the images estimated by the reconstruction. More specifically, the forward model, F(x), is a function defined such that E[y]=F(x). In one embodiment, a simplifying approximation is made such that $E[y_k]=F(x_k)$.

Accordingly, and in the exemplary embodiment, an iterative reconstruction algorithm may be utilized to reconstruct an image utilizing a multislice CT reconstruction system. IR algorithms are utilized to determine the unknown value of x by searching for the value of the vector x that best matches the measured data. In the exemplary embodiment, this is accomplished utilizing a cost function of the form:

$$\hat{x} = \operatorname*{argmin}_{x}\{D(y, F(x))\} \quad (1)$$

where $\hat{x}$ is the value of the variable x which achieves the minimum of the function, and D(y,F(x)) is a function which increases when y and F(x) differ greatly. In the exemplary embodiment equation (1) can be minimized in a variety of manners using optimization methods such as, but not limited to, iterative coordinate descent, expectation maximization, conjugate gradient, and/or any number of alternative techniques.

However, the solution to equation (1) is often too noisy. More specifically, the noise may appear when there are two few measurements, when the quality of the measurements is poor, and/or when the available projection angles and locations do not provide sufficient information about x to properly reconstruct it.

Accordingly, at least one known method utilized for a multislice CT system adds an additional stabilizing functional S(x) to the cost function being minimized. However, this results in the regularized inverse shown in equation 2.

$$\hat{x} = \operatorname*{argmin}_{x}\{D(y, F(x)) + S(x)\} \quad (2)$$

where, the function S(x) is generally selected to penalize spatial variations in three dimensions. However, the three-dimensional iterative reconstruction shown in equation (2) is relatively complex since it requires the optimization of a function with a three-dimensional input.

One possible simplification of equation 2 is to approximately reformulate the iterative reconstruction in two dimensions. For example, a single plane or slice can be reconstructed independently of other slices as shown in equation 3.

$$\hat{x}_k = \operatorname*{argmin}_{x_k}\{D_k(y_k, F(x_k)) + S_k(x_k)\} \quad (3)$$

However, this form of two-dimensional iterative reconstruction shown in equation 2 has two disadvantages. First, the forward model is approximated because the true projections pass through more than a single slice of x. Second, the stabilizing function, $S_k(x_k)$, can only penalize variations in two dimensions, rather than the full three dimensions. Accordingly, the two-dimensional reconstruction shown in equation 3 may degrade the quality of two-dimensional iterative reconstructions.

Accordingly, and in the exemplary embodiment, a 2.5 dimensional iterative reconstruction algorithm for a multislice CT system, such as system 10, is generated. In the exemplary embodiment, the 2.5 dimensional iterative reconstruction algorithm combines the two-dimensional forward model with the three-dimensional prior model to generate the 2.5 dimensional iterative reconstruction algorithm. In the exemplary embodiment, the 2.5 dimensional iterative reconstruction algorithm generates an image that has an increase quality compared to the two-dimensional algorithm, while utilizing a reduced quantity of computations compared to the three-dimensional algorithm. In the exemplary embodiment, the 2.5 dimensional iterative reconstruction algorithm is defined as:

$$\hat{x} = \operatorname*{argmin}_{x}\left\{\sum_{k=0}^{K_1} D_k(y_k, F(x_k)) + S(x)\right\} \quad (4)$$

where $D_k(y_k, F(x_k))$ is the data term associated with the kth slice, and S(x) is a stabilizing function that panelizes variations in three dimensions.

In the exemplary embodiment, the 2.5 dimensional iterative reconstruction algorithm described herein retains the benefits of the true three-dimensional regularization prior, which enforces a smoothness penalty on the reconstructed images in order to significantly improve image quality, while conserving the simple two-dimensional forward model that can be leveraged for fast practical implementations of iterative image reconstruction using this approach.

More specifically, the dimensions of the fully three-dimensional forward model prohibit the storage of the system matrix represented by F. For example, the inability of the system to store the fully three-dimensional model reduces reconstruction speed which is a feature critical to practical implementation. Accordingly, the 2.5 dimensional iterative reconstruction algorithm described herein allows faster reconstruction compared to the fully three-dimensional model, while also conserving the advantages in image quality of a fully developed regularization. Moreover, the 2.5 dimensional iterative reconstruction algorithm may facilitate reducing the dosage of radiation received by the patient during the scanning procedure, reduce artifacts, and edge preservation for resolution recovery over a purely two-dimensional method.

The method described herein allows for iterative reconstruction from multislice CT data that has increased quality relative to known two-dimensional reconstruction algorithms, and also requires fewer computations compared to known three-dimensional reconstruction algorithms.

Figure 3:
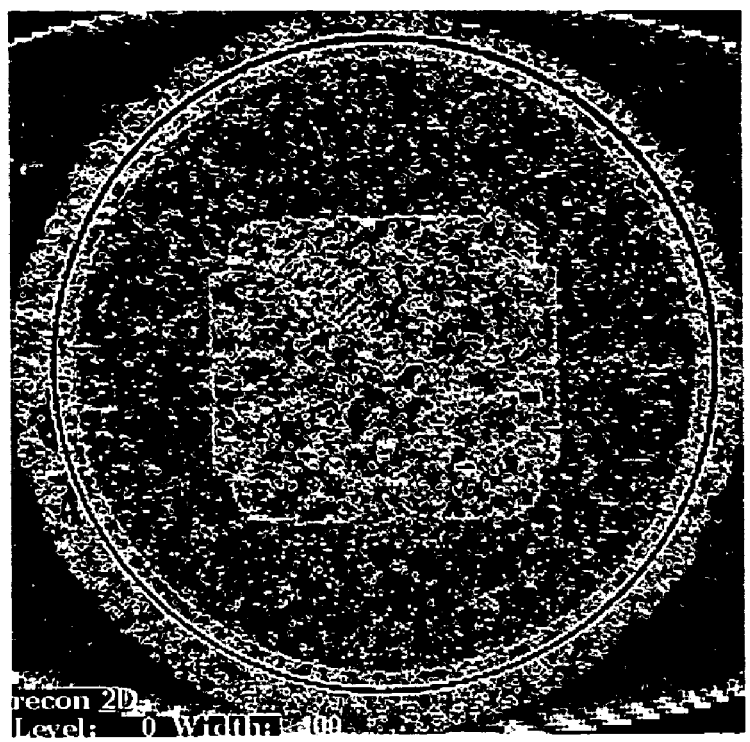
FIG. 3 is a CT image that is generated utilizing a 2-dimensional algorithm.
Figure 4:
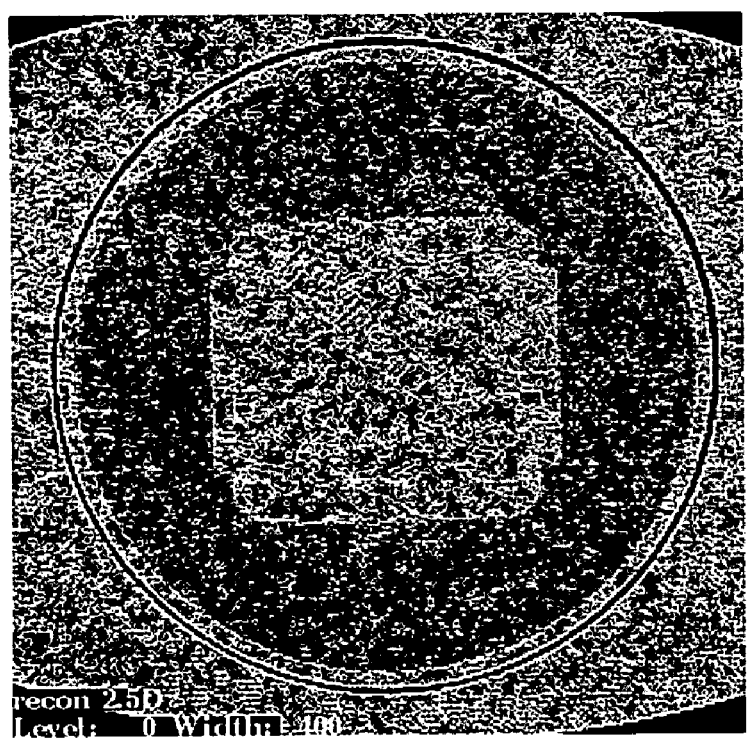
FIG. 4 is a CT image that is generated utilizing a 2.5-dimensional algorithm.

FIG. 3 is an image generated utilizing a two-dimensional algorithm. FIG. 4 is an image generated utilizing the novel 2.5-dimensional algorithm described herein. Specifically, FIG. 3 is an image of a QA phantom that is inserted into an oval body phantom that is generated utilizing a two-dimensional iterative reconstruction algorithm, and FIG. 4 is an image of the same phantom shown in FIG. 3 that is reconstructed using the 2.5 dimensional iterative reconstruction described herein, which illustrates a reduction of the horizontal deep streaking artifacts compared to those shown in FIG. 3.

Described herein is an algorithm that combines a full three-dimensional stabilizing function with a two-dimensional forward model for each slice of CT data. Known reconstruction techniques utilize a full three-dimensional iterative reconstruction technique that is accomplished using a three-dimensional forward model, and a two-dimensional iterative reconstruction has been done with a two-dimensional stabilizing function. Combining the two-dimensional and three-dimensional modeling techniques to perform 2.5D iterative reconstruction facilitates reducing the computations required compared to three-dimensional iterative reconstruction and also substantially increases image quality compared to known two-dimensional iterative reconstruction techniques.

While the invention has been described in terms of various specific embodiments, those skilled in the art will recognize that the invention can be practiced with modification within the spirit and scope of the claims.

What is claimed is:

1. A method of reconstructing an image, said method comprising:
    combining a two-dimensional forward projection function and a three-dimensional stabilizing function to generate an iterative reconstruction algorithm; and
    using the obtained iterative reconstruction algorithm to perform a multislice Computed Tomography (CT) reconstruction to generate an image.

2. A method in accordance with claim 1 wherein combining a two-dimensional forward projection function and a three-dimensional stabilizing function to generate an iterative reconstruction algorithm further comprises combining a two-dimensional forward function of the form $D_k(y_k, F(x_k))$ and a three-dimensional stabilizing function of the form $S(x)$ to generate an iterative reconstruction algorithm in the form of $$\hat{x} = \underset{x}{\operatorname{argmin}} \left\{ \sum_{k=0}^{K_1} D_k(y_k, F(x_k)) + S(x) \right\},$$

wherein $D_k(y_k, F(x_k))$ is a term associated with the kth slice.

3. A method in accordance with claim 2, wherein $S(x)$ penalizes differences among spatially adjacent components of x.

4. A method in accordance with claim 2, wherein $D_k(y_k, F(x_k))$ is associated with a slice which is oblique to horizontal or vertical lines.

5. A method in accordance with claim 2, wherein $$\left\{ \sum_{k=0}^{K_1} D_k(y_k, F(x_k)) + S(x) \right\}$$

is minimized using at least one of an iterative coordinate descent technique, an expectation maximization technique, a gradient technique and a conjugate gradient technique.

6. A method in accordance with claim 2, wherein $D_k(y_k, F(x_k))$ is a distance between $y_k$ and $F(x_k)$.

7. A method in accordance with claim 2, wherein $D_k(y_k, F(x_k))$ penalizes a function of the probability of observing $y_k$ when $x_k$ is the k-th slice.

8. An imaging system comprising:
    a radiation source;
    a detector array comprising a plurality of cells positioned to receive radiation from said source; and
    a computer coupled to said detector array; said computer configured to:
    combine a two-dimensional forward projection function and a three-dimensional stabilizing function to generate an iterative reconstruction algorithm; and
    use the obtained iterative reconstruction algorithm to perform a multislice Computed Tomography (CT) reconstruction to generate an image.

9. An imaging system in accordance with claim 8, wherein said computer is further configured to combine a two-dimensional forward function of the form $D_k(y_k, F(x_k))$ and a three-dimensional stabilizing function of the form $S(x)$ to generate an iterative reconstruction algorithm in the form of $$\hat{x} = \underset{x}{\operatorname{argmin}} \left\{ \sum_{k=0}^{K_1} D_k(y_k, F(x_k)) + S(x) \right\},$$

wherein $D_k(y_k, F(x_k))$ is a term associated with a kth slice.

10. An imaging system in accordance with claim 9 wherein $S(x)$ penalizes differences among spatially adjacent components of x.

11. An imaging system in accordance with claim 9 wherein $D_k(y_k, F(x_k))$ is associated with a slice which is oblique to horizontal or vertical lines.

12. An imaging system in accordance with claim 9 wherein $$\left\{ \sum_{k=0}^{K_1} D_k(y_k, F(x_k)) + S(x) \right\}$$

is minimized using at least one of an iterative coordinate descent technique, an expectation maximization technique, and a conjugate gradient technique.

13. An imaging system in accordance with claim 9, wherein $D_k(y_k, F(x_k))$ is a distance between $y_k$ and $F(x_k)$.

14. An imaging system in accordance with claim 9, wherein $D_k(y_k, F(x_k))$ penalizes a function of the probability of observing $y_k$ when $x_k$ is the k-th slice.

15. A computer readable medium encoded with a program configured to instruct a computer to:
    combine a two-dimensional forward projection function and a three-dimensional stabilizing function to generate an iterative reconstruction algorithm; and
    use the obtained iterative reconstruction algorithm to perform a multislice Computed Tomography (CT) reconstruction to generate an image.

16. A computer readable medium in accordance with claim 15, wherein said program is further configured to instruct the computer to combine a two-dimensional forward function of the form $D_k(y_k, F(x_k))$ and a three-dimensional stabilizing function of the form $S(x)$ to generate an iterative reconstruction algorithm in the form of $$\hat{x} = \underset{x}{\operatorname{argmin}} \left\{ \sum_{k=0}^{K_1} D_k(y_k, F(x_k)) + S(x) \right\},$$

wherein $D_k(y_k, F(x_k))$ is a term associated with a kth slice.

17. A computer readable medium in accordance with claim 15 wherein $S(x)$ penalizes differences among spatially adjacent components of x.

18. A computer readable medium in accordance with claim 15 wherein $D_k(y_k, F(x_k))$ is associated with a slice which is oblique to horizontal or vertical lines.

19. A computer readable medium in accordance with claim 15, wherein $$\left\{ \sum_{k=0}^{K_1} D_k(y_k, F(x_k)) + S(x) \right\}$$

is minimized using at least one of a iterative coordinate descent technique, an expectation maximization technique, and a conjugate gradient technique.

20. A computer readable medium in accordance with claim 15, wherein $D_k(y_k, F(x_k))$ penalizes a function of the probability of observing $y_k$ when $x_k$ is the k-th slice.

* * * * *